(12) United States Patent
Laible et al.

(10) Patent No.: US 9,963,709 B2
(45) Date of Patent: May 8, 2018

(54) **TRANSFORMABLE *RHODOBACTER* STRAINS, METHOD FOR PRODUCING TRANSFORMABLE *RHODOBACTER* STRAINS**

(75) Inventors: Philip D. Laible, Villa Park, IL (US); Deborah K. Hanson, Villa Park, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 428 days.

(21) Appl. No.: 13/619,406

(22) Filed: Sep. 14, 2012

(65) Prior Publication Data
US 2014/0080176 A1   Mar. 20, 2014

(51) Int. Cl.
C12N 15/74 (2006.01)
C12P 21/02 (2006.01)
C12N 9/22 (2006.01)

(52) U.S. Cl.
CPC ............... *C12N 15/74* (2013.01); *C12N 9/22* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 6,465,216 B2 | 10/2002 | Laible et al. | |
| 2003/0170775 A1* | 9/2003 | Pompejus et al. | 435/66 |
| 2006/0063239 A1* | 3/2006 | Klopprogge et al. | 435/106 |
| 2007/0092943 A1* | 4/2007 | Laible | C12N 15/74 435/69.1 |
| 2007/0185016 A1* | 8/2007 | Muir et al. | 514/9 |
| 2008/0118959 A1* | 5/2008 | Schroder et al. | 435/113 |
| 2014/0221251 A1* | 8/2014 | Bramhill et al. | 506/14 |

OTHER PUBLICATIONS

C. S. Fornari, et al., Genetic Transformation of Rhodopseudomonas sphaeroides by Plasmid DNA, Journal of Bacteriology, (Oct. 1982), pp. 89-97.
T.J. Donohue, et al., Genetic Techniques in Rhodospirillaceae, Methods in Enzymology, vol. 204, (1991), pp. 459-486.
Mackenzi et al, Annu. Rev. Microbiol (2007), 61, 283-307.
Choudhardy et al. J. Bacteriol. (2007) 189(5): 1914-1921.

* cited by examiner

Primary Examiner — Nancy A Treptow
(74) Attorney, Agent, or Firm — Cherskov Flaynik & Gurda, LLC (57) ABSTRACT

The invention provides an organism for expressing foreign DNA, the organism engineered to accept standard DNA carriers. The genome of the organism codes for intracytoplasmic membranes and features an interruption in at least one of the genes coding for restriction enzymes. Further provided is a system for producing biological materials comprising: selecting a vehicle to carry DNA which codes for the biological materials; determining sites on the vehicle's DNA sequence susceptible to restriction enzyme cleavage; choosing an organism to accept the vehicle based on that organism not acting upon at least one of said vehicle's sites; engineering said vehicle to contain said DNA; thereby creating a synthetic vector; and causing the synthetic vector to enter the organism so as cause expression of said DNA.

5 Claims, 6 Drawing Sheets

TRANSFORMABLE *RHODOBACTER* STRAINS, METHOD FOR PRODUCING TRANSFORMABLE *RHODOBACTER* STRAINS

CONTRACTUAL ORIGIN OF THE INVENTION

The U.S. Government has rights in this invention pursuant to Contract No. DE-AC02-06CH11357 between the United States Government and UChicago Argonne, LLC, representing Argonne National Laboratory.

BACKGROUND OF THE INVENTION

1. Field of the Invention

This invention relates to a user-friendly transformable bacteria and production of biological molecules using the transformable bacteria, and specifically this invention relates to a mutant strain of *Rhodobacter* bacteria capable of uptake and maintenance of heterologous DNA. One application uses invented mutant strains for efficient production of biological molecules.

2. Background of the Invention

The search continues for rapid and efficient means to harness biological systems to produce complex molecules. A myriad of molecule types are targeted for more rapid and efficient production, including but not limited to feedstocks, nutrients, membrane proteins, drop-in fuel moieties, nutraceuticals, specialty chemicals, and precursors of bio-based polymers.

Membrane proteins are particularly relevant targets given their potential as drug development templates. Biological membranes serve as the interface between living matter and the environment. Membranes also separate functional compartments within complex cells. Some organisms produce intracellular membranes which are used to divide cells into functional and structural compartments such as organelles, vacuoles, nuclear envelopes, etc. In *Rhodobacter*, intracytoplasmic membranes (ICMs) can be induced to form and simultaneously encapsulate heterologously-expressed membrane proteins. The inventors developed and previously disclosed this system in U.S. Pat. No. 6,465,216 which is incorporated in its entirety by reference.

Proteins inserted in membranes carry out essential biological processes including uptake of nutrients, excretion of wastes, signal transduction, response to external stimuli, and energy conversion reactions. Genes encoding membrane proteins represent approximately 30 percent of every genome. Membrane proteins comprise the majority (up to 80 percent by some industrial estimates) of the drug targets that are being pursued currently.

Most drugs are targeted at G-protein coupled receptors (GPCRs), a class of integral membrane proteins for which there is little structural information. The human genome encodes approximately 800 unique GPCRs, and annual world-wide GPCR-targeting drug sales exceed $250 billion. The impact of an efficient membrane protein expression system in the process for discovery of just a single new GPCR-targeting drug could yield substantial revenue.

In addition, markets for bioengineered crop plants have expanded 10 percent annually over the last 10 years, signifying increased global acceptance. Membrane protein expression technology has the potential to enable and speed certification processes for engineered food crops.

Also, procedures for producing next-generation biofuels use enzymatic reactions that are catalyzed by membrane proteins. The impact of an efficient membrane protein expression system on processes to replace petroleum-based fuels will generate large revenue streams.

Membrane proteins are lipid soluble, and therefore require hydrophobic environments for stability and functional integrity. As such, their abundance in native cells or tissues is often very low. Structure determination—that can be used as an important input for rational drug design—for membrane proteins lags far behind that known for soluble proteins by approximately a 100:1. Thus, expression technology leading to the acquisition of structural information is needed for this important target class.

Researchers require milligram quantities of membrane proteins in their native configurations) to adequately study membrane protein structure and function. Every viable strategy for structure/function studies of membrane proteins is dependent upon an efficient means for membrane protein production.

Commercial expression systems are available that are based on the use of prokaryotic hosts *E. coli, Bacillus subtilis*, and *Lactococcus lactis*; these systems excel in the production of soluble proteins. More versatile systems that are capable of post-translational modification of expressed proteins (e.g., glycosylation, etc.) use yeast expression hosts. Commercial yeast expression systems employed for soluble proteins include those based on *Saccharomyces cerevisiae, Pichia pastoris*, and *Kluyveromyces lactis*. All of the above organisms are easily cultured on inexpensive media but are not designed for the expression of membrane proteins because they lack inducible membranes that can sequester newly expressed protein.

Unlike the above mentioned prokaryotes, *Rhodobacter* is an efficient membrane producer. However, *Rhodobacter* strains are not amenable to chemical transformation or electroporation so as to enable simple generation of expression strains to produce heterologous proteins. The barrier to the introduction of plasmid DNA in host organisms such as *Rhodobacter* is that they encode enzymes of DNA restriction-modification systems as protection against foreign DNA. The modification enzymes 'mark' the cell's own DNA by methylating it to differentiate it from other DNA in the environment. This allows the restriction endonucleases to 'restrict' or destroy any double-stranded DNA which enters the cell that is not marked appropriately. All strains of *E. coli* that are used commonly as cloning and expression hosts have been genetically modified to remove these endogenous restriction-modification enzymes to enable successful transfer and maintenance of foreign DNA in the cells.

The standard method for introduction of foreign DNA comprises incubation of pure DNA with chemically-treated cells to "transform" them to a selectable phenotype that is encoded by a gene on the segment of pure plasmid DNA. In some transformation protocols, the efficiency of this process is increased by application of an electric current, resulting in transformation via "electroporation".

At present, neither chemical nor electroporetic transformation of *Rhodobacter* with pure double-stranded plasmid DNA is generally possible. Previous efforts, such as Formari et al *J. Bacteriol* 152, 89-97 disclosed that chemically competent *R. sphaeroides* has been transformed with double-stranded plasmid DNA which lack sequences recognized by endogenous restriction enzymes—a limited approach as most plasmids have these sequences. Other researchers, Donohue, T. J. et al *Methods in Enzymology*, 204, pp. 459-486 (1991), have transformed electro-competent *R. sphaeroides*. However, as with chemical transformation discussed supra, electrotransformation was successful only when plasmids lacking sites for endogenous restriction enzymes were used.

Again, since most expression plasmids have these sequences and most genes of foreign proteins one desires to express are likely to have these sequences, it has been necessary to introduce DNA by transferring expression plasmids to *Rhodobacter* strains via conjugal mating with an appropriate *E. coli* donor strain. In this process, depicted in FIG. 1, cells of the *E. coli* strain carrying the plasmid DNA are mixed with cells of the *Rhodobacter* recipient strain. The DNA from the *E. coli* donor strain enters the *Rhodobacter* host in a single-stranded form that is not susceptible to endogenous restriction endonucleases. (Thus the foreign DNA is not cleaved and transfer is successful.) Endogenous modification enzymes originating from within the organism methylate, "mark", or otherwise protect the incoming DNA concomitantly with its replication to form double-stranded DNA.

Figure 1:
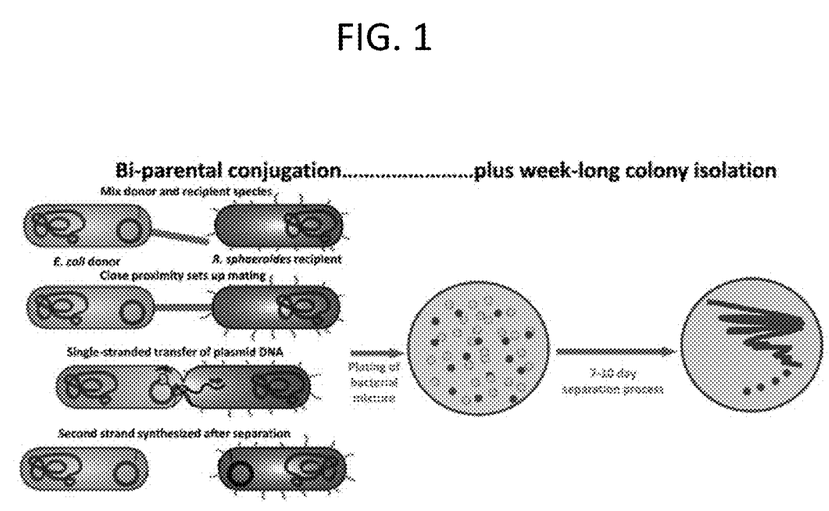
FIG. 1 depicts the state of the art process of bacterial conjugation and the process of purification of *Rhodobacter* transconjugants from a mixed population of donor and recipient organisms.

Unfortunately, the conjugation depicted in FIG. 1 is time-consuming due to the subsequent requirement for performing multiple rounds of colony growth to purify the desired *R. sphaeroides* transformants from the *E. coli* donor cells. Repeated re-streaking and growth of single colonies on agar plates can take up to 10 days. Also, these steps cannot be automated or adapted easily to be compatible with higher-throughput cloning and expression procedures. Conjugation techniques are rarely used in typical molecular biology laboratories. As such, this step in the process of using *Rhodobacter* as an expression vehicle requires special training and is viewed as cumbersome for the general user.

As noted supra, the inventors previously developed a system whereby plasmid vectors are utilized to induce *Rhodobacter* bacteria to simultaneously produce, and sequester heterologous protein. However, and as noted supra, transfer of the constructed expression plasmid to the host cell via conjugation is a time-consuming and technically-challenging step requiring specialized training of the laboratory worker.

A need exists in the art for an easily used system for the production of biological moieties which generates milligram quantities of target moiety per liter of culture. The system should be capable of being incorporated into a kit, operational within 1-2 days, and does not require high level of skills in the art. The system should be operable with standard vectors, and transportable in frozen state prior to use.

SUMMARY OF INVENTION

An object of the invention is to provide a transformable organism and a method to produce such an organism for use in the expression of heterologous protein.

Another object of the invention is to provide a method for producing transformed *Rhodobacter*, which would then serve as a host for producing target moieties A feature of the invention is that the host is engineered, not the vector. An advantage of the invention is that gene sequences of the native host that are detrimental to the entry and maintenance of foreign DNA are removed.

Still another object of the present invention is to provide a transformable *Rhodobacter* strain. A feature of the invention is that the genome of the transformed *Rhodobacter* has deleted from it genes encoding endogenous restriction enzymes. An advantage of the invention is that the deletion eliminates concern for the presence of restriction enzyme recognition sites found in any gene or vehicle used for transformation such that the expression system can be employed with any expression vehicle that has been designed by a particular user.

Another object of the present invention is to provide a mutant bacterium to facilitate expression of heterologous genetic material. A feature of the invention is that a myriad of standard cloning and expression vectors (both replicatable and nonreplicatable in *Rhodobacter*) are accommodated by the mutant. An advantage of the invention is that the expression strain is generated immediately as compared to the 7-10 days required previously for production of an expression strain via conjugation methods. Another advantage of the invention is that automatic, multiwell-plate based production methods can be utilized for higher throughput of target biological moieties in very short periods of time as colony purification on plates is no longer necessary.

Yet another object of the present invention is providing competent *Rhodobacter* cells for both chemical and electroporetic transformation. A feature of the invention is that the recombinant strain is produced directly and can be transferred immediately to broth (and takes only about 48 hours if one desires to proceed from a single colony). An advantage of the invention is that production of target moieties is expedited, and can be completed by technicians with limited training, thereby resulting in efficient and cost-effective production of target moieties. The ability to use frozen aliquots of previously prepared chemically- or electroporetically-competent cells (the frozen aliquots of which have at least six month shelf lives) reduces even more the time needed to generate recombinant strains and would make *Rhodobacter* as convenient an expression vehicle as *E. coli* is today.

Still another object of the present invention is to provide an engineered membrane protein production system that is at least as efficient as state of the art engineered membrane protein production systems. A feature of the invention is that the engineered system can express heterologous DNA introduced by standard vectors. An advantage of the engineered system is that it can be manufactured immediately in culture broth or within 24 to 48 hours if the broth is to be plated for individual colonies. The engineered bacterium generates between about 100 and 1000 transformants per microgram of DNA. An embodiment of the invention is that these expression strains are capable of yielding target proteins in excess of 10 milligrams per liter of culture.

Briefly, the invention provides an organism for expressing foreign DNA, the organism engineered to accept standard DNA carriers. For example, the invention provides a bacterium comprising *Rhodobacter* that simultaneously produces intracytoplasmic membranes and foreign moieties within the membranes, wherein the *Rhodobacter* host is modified to accept carriers of the DNA encoding the foreign moieties so as to produce and sequester the foreign moieties, if needed. The genome of the organism coding for intracytoplasmic membranes features an interruption or modification in the genes coding for restriction/modification enzymes or the regulatory element(s) which control their expression. A means for not coding the restriction enzymes includes modifying the genome to have an interruption, partial or full deletion of a gene coding for at least one of the restriction enzymes.

The invention provides a method for transforming a membrane-elaborating organism which can be used for producing and sequestering large quantities of biological molecules, the method comprising selecting a DNA vector to carrying DNA which encodes the biological molecules; inserting that vector into the organism to allow the organism to produce the biological molecules, wherein the organism lacks the ability to destroy the DNA encoding the biological molecules.

Also provided is a method for creating a transformable organism that can be used for sequestering large quantities of heterologous protein, the method comprising selecting a vector as a vehicle for DNA encoding the protein; determining sites in the hybrid vehicle's sequence that are susceptible to cleavage by enzymes of the host's restriction-modification system; inactivating genome-localized, endogenous genes encoding host restriction enzymes to prevent said cleavage; modifying said vector to contain DNA encoding the target heterologous protein; thereby creating a synthetic vector; and transforming the organism with the synthetic vector as reflected by the gain of plasmid-borne antibiotic resistance.

The invention further provides a system for producing biological materials, the system comprising: selecting a vehicle to carry DNA which codes for the biological materials; determining sites on the vehicle's DNA sequence susceptible to restriction enzyme cleavage; choosing an organism to accept the vehicle based on that organism not acting upon at least one of said vehicle's sites; engineering said vehicle to contain said DNA; thereby creating a synthetic vector; and causing the synthetic vector to enter the organism so as cause expression of said DNA.

The invention also provides a method for creating and maintaining expression hosts in a state competent for the uptake of DNA which encodes for biological molecules, the method comprising supplying an organism capable of producing intracytoplasmic membranes; freezing the organism so as to allow for transport to a location where the creation of the biological molecules takes place, wherein the organism can remain competent in the frozen state for at least 180 days; transporting the frozen organism to the location; thawing the frozen organism; inserting the DNA into the thawed organism; and allowing the thawed organism to produce the biological molecules.

The invention also provides a kit for expressing heterologous protein, the kit comprising an organism capable of producing intracytoplasmic membrane; modification to the genome of the organism such that at least one gene encoding for endogenous restriction enzyme is deactivated; and means of ingress to the organism to allow a vector containing DNA encoding the protein to enter the organism and cause expression of the protein. The means of ingress are treatments that render the outer membranes and cell wall permeable, enabling the organism to be transiently receptive/competent for the uptake of DNA. The permeability is achieved with chemicals, with an applied electric field or both. The competent organism has a shelf life of at least six months when frozen. The vector is capable of replication in *Rhodobacter*. or conversely is incapable of replication in *Rhodobacter*. The vector is a fragment of DNA, lacking an origin of replication. The fragment can be generated by the polymerase chain reaction. Also the fragment is generated by restriction enzyme digestion.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The inventors envisioned a more efficient approach to making bacteria an industrial-scaled vehicle for producing heterologous protein via engineering of the bacterium's genome. The invention enables transformation of chemical- or electro-competent hosts. It is intended to render the organism capable of direct transformation by deleting genes from the host's genome that encode endogenous restriction enzymes. Deletion of the genes encoding these enzymes eliminates concern about sites for endogenous restriction endonucleases in any gene that might be cloned in existing or future versions of platform vectors. Specifically, the invention conserves desired features of an organism, e.g., the intracytoplasmic membranes that sequester expressed membrane proteins but removes undesired features, such as restriction enzymes.

A new *Rhodobacter* deletion strain ΔrshI has been constructed so as to be efficiently transformed by common laboratory methods. These methods include chemical or electrical means to introduce DNA into competent cells. Yields of between approximately 100 and 1000 transformants per microgram are obtained. Moreover, the engineered strain is capable of withstanding freezing, transport, and subsequent thawing for use at production sites remote from the point of manufacture of the strain. Thawed organisms provide a yield of transformants which is at least 50 percent that obtained with freshly competent cells. The organisms can be stored for at least six months without significant reduction in the aforementioned 50 percent yield.

Further improvement in transformation efficiency is obtained by generating and employing electro-competent R. sphaeroides cells and protocols. Through these collective improvements, it is anticipated that the engineered Rhodobacter expression system will be more amenable to high-throughput methodologies and multiwell-plate-based protocols, and its utility as an expression vehicle for membrane proteins will expand.

Figure 2:
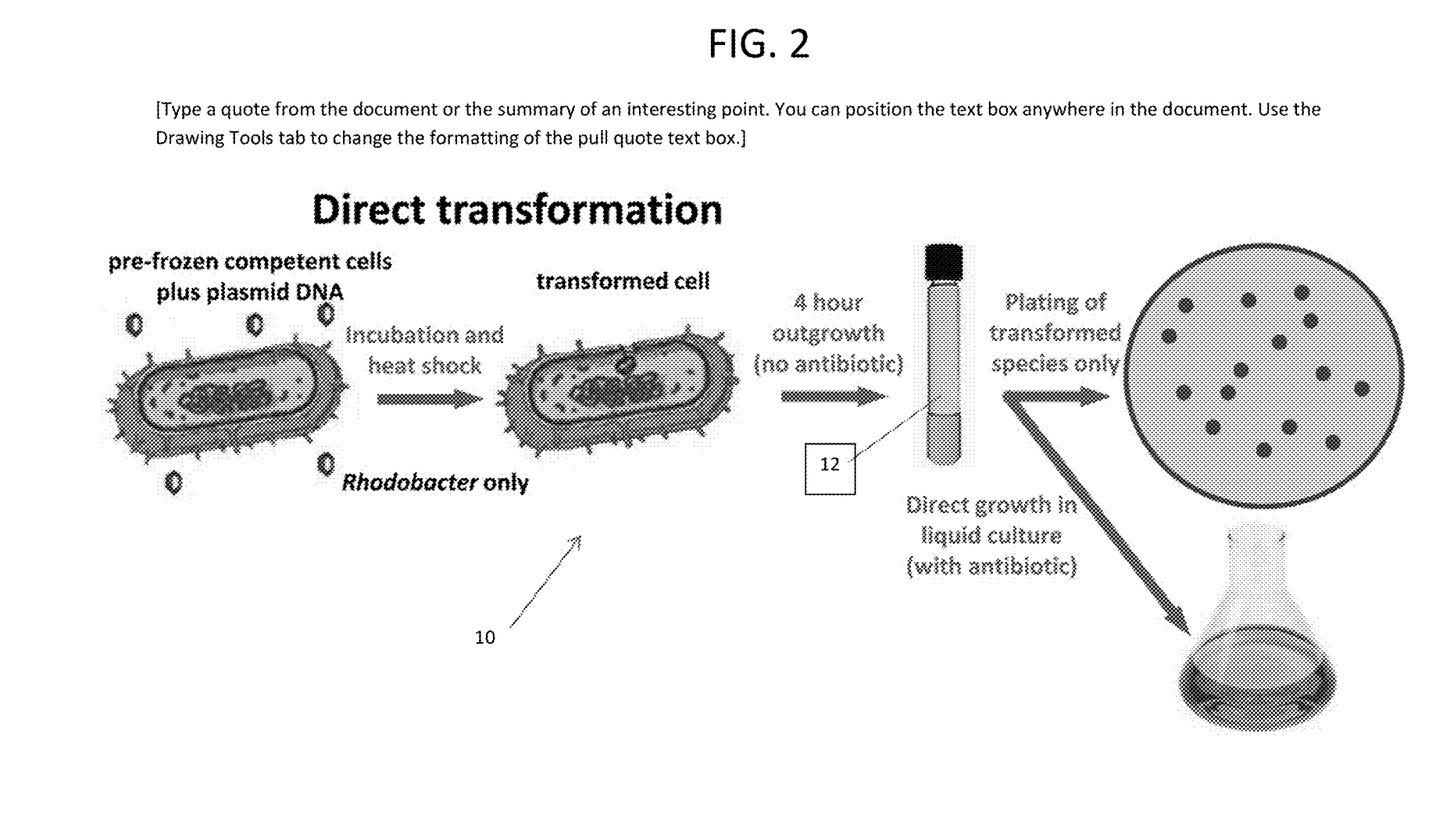
FIG. 2 depicts a process for chemical transformation of bacteria, in accordance with features of the present invention.

As depicted in FIG. 2, an embodiment of the invention employs transformation, designated as numeral 10. This embodiment provides an engineered R. sphaeroides host strain receptive to the uptake and maintenance of any plasmid DNA that carries foreign protein genes and the genetic elements that direct their expression. Genes encoding host cell enzymes that destroy foreign DNA are deleted, or otherwise inactivated. This embodiment yields direct growth in a liquid culture 12. This embodiment obviates the need for a relatively longer process of plating to obtain a single colony.

The instant mutant improves the membrane protein expression system disclosed in the aforementioned '216 patent. That system enabled expression of the target protein gene under control of a promoter that responds to the same environmental cues as ICM synthesis. This enabled tight coupling of the expression of the target membrane protein with production of new membrane that isolates, or otherwise contains it. This feature ensured that the newly-expressed membrane protein was immediately inserted into a membrane, preventing the denaturation, aggregation and precipitation that are often the fate of membrane proteins expressed within host cells of other species which do not contain intracytoplasmic membranes.

The instant expression strain mutant is generated directly upon chemical or electrophoretic transformation. For those who use protocols wherein expression strains are first streaked and isolated on agar, the expression strain is isolated from a single colony within two days. This compares with the 10 days necessary in the first, aforementioned engineered system.

An embodiment of the invention enables the successful expression of hundreds of foreign target proteins using an engineered prokaryotic bacterial membrane protein expression system. As examples of this engineering, genes encoding at least eleven restriction-modification systems have been identified in the R. sphaeroides genome sequence and are targets for deactivation, via interruption (e.g., transposon mutagenesis or mutagenic agents eliciting random DNA modification), via partial deletion or complete deletion of the gene's regulatory elements or coding sequence.

An initial target is the rshI gene because six sites that are recognized by restriction enzyme RshI are present in platform vectors used for expression in the in vivo membrane protein expression systems. Those vectors are enumerated infra.

Transformation is facilitated with plasmids, including but not limited to pMEMS1, and also pRKPLHT1 as disclosed in Laible et al. 2009 Springer, 839-860, pertinent pages of which are incorporated herein by reference. These vectors facilitate a much shorter build time of the instant expression strain. These vectors also allow a lesser trained technician to make the strain. In the absence of a transformable host strain, conjugation is used to transfer the expression plasmid.

A segment of DNA is constructed in vitro wherein a gene encoding antibiotic resistance is flanked by segments identical to sequences that are located upstream and downstream of the target gene on the bacterial chromosome. This engineered plasmid is transferred to the host strain via conjugation and homologous recombination between the identical sequences on the plasmid with those that flank the gene of interest on the chromosome result in replacement of the target gene with the antibiotic resistance gene 56. Selection for growth on that antibiotic is the first step in isolating and confirming candidate deletion strains. Presence of the deletion is then verified for candidate colonies by using the polymerase chain reaction (PCR) with diagnostic oligonucleotide primers.

A salient feature of the invention is that genes encoding host cell enzymes that destroy incoming foreign DNA are deleted. In an embodiment of the invention the host cell is R. sphaeroides. The rshI gene was the initial gene targeted for deletion. This gene encodes the restriction endonuclease RshI that cleaves DNA within the recognition sequence CGATCG if it is not 'marked' specifically with the host cell's methylation pattern. Six sites that are recognized by RshI are present in the expression vectors used for production of candidate membrane proteins. These plasmids—which are engineered using organisms other than Rhodobacter—are recognized as 'foreign' when inserted using common biochemical methods (such as chemical transformation or electroporation) into cells of the Rhodobacter host strain. As discussed supra, these plasmids are not cleaved and destroyed when they are inserted using a time-consuming process that involves conjugal transfer of single-stranded DNA to Rhodobacter via an E. coli donor strain.

To facilitate deletion ('knockout') of the rshI gene via a double crossover approach (FIG. 3A), four DNA components were combined to form a DNA segment, also known as a 'cassette'. This cassette is depicted in FIG. 3B as element number 54. Those four components comprise upstream and downstream segments that flank the target gene (e.g. rshI), a gene encoding gentamicin resistance, and loxP sites as carried in a plasmid that is capable of replication in E. coli but not in Rhodobacter. The flanking segments upstream (partially including RSP_3757, a gene of unknown function) and downstream (encompassing RSP_3758, a gene of unknown function) of the rshI gene on the bacterial chromosome were amplified from R. sphaeroides genomic DNA using the polymerase chain reaction (PCR). The gentamicin resistance gene was amplified from plasmid pBBR1MCS-5 and was bordered by loxP sites.

The array of antibiotic resistance genes 56 for use in R. sphaeroides is limited, especially so since two have already been used to facilitate production of foreign membrane proteins in the starting host strain ΔΔ11. Thus, the construct was engineered to enable 'recycling' of the gentamicin resistance marker for its repeated use in constructing multiple gene deletions in the organism. The cre/lox system allows for site-specific deletions of genes flanked by loxP recognition sites. By inserting the gentamicin resistance marker gene flanked by loxP sites in place of a gene targeted for knockout, the antibiotic resistance marker gene can be excised by Cre recombinase and used again as a selectable marker in the deletion of additional genes. The 'cassette' combining all of these elements is then cloned into a plasmid vector that directs incorporation of the synthetic cassette into the bacterial chromosome (FIG. 3B).

Example 1

Construction of Deletion Strain Detail

Engineered plasmid 52 is transferred to the *R. sphaeroides* host strain ΔΔ11 via conjugation, 55. Homologous recombination between the identical sequences on the plasmid with those that flank the rshI gene on the chromosome results in replacement of the target gene with the gentamicin resistance gene (FIG. 3A). Selection for growth on gentamicin was the first step in selecting candidate deletion strains, and their appearance indicated that deletion of the rshI gene was not lethal for the organism. The presence of the deletion in genomic DNA derived from candidate colonies was confirmed via PCR with diagnostic oligonucleotide primers.

The inventors targeted the rshI gene for deletion. This gene encodes a Type II restriction enzyme that cleaves at the recognition sequence CGATCG. This sequence is found in multiple occurrences in the expression vector that are used for the *Rhodobacter* membrane protein expression system and can occur frequently in the genes of proteins that are targeted for expression in this system. The design and construction of this engineered strain will be described in detail. Descriptions of the design and construction of other knock-outs and multiply-mutated strains are similar but not included here within.

The entire gene sequence for the *Rhodobacter* engineered by the inventors is found at the American Type Culture Collection as deposit number ATCC 17025. That sequence is also discussed in Mackenzi et al, *Annu. Rev. Microbiol* (2007), 61, 283-307, and Choudhardy et al. *J. Bacteriol.* (2007) 189(5): 1914-1921, both papers of which are incorporated by reference.

The gene sequence for the restriction enzyme RshI (RSP 3759) was deleted from the engineered *Rhodobacter* genome. The gene resides on Chromosome 2 and lies on the complement of the sequence that spans positions 884950 to 885807. In other words, viewing the position of the gene as the complement of Chromosome 2, the beginning point of the gene is 885807, and the end point is 884950. The restriction enzyme sequence (5'→3') is as follows:

```
                                         (SEQ ID NO: 1)
ATG GCT GAT CCT GAA CCC GAG AAC GTT TCG GCA GAA

GCC CAG GCG GCC GTC ACT TCC GCC GAG CCG AAG ACA

TTG AAC GCC TAT CAG GCG ATC ATC GTC GAC ATC TTC

CAA CGG TTC TAT CGG CCG GGC ATG GAG GAG TTC GAG

TTC GGC CGC GAG GAA ATC TAC GAG GCC GCC GTC AGG

ACG GGC GTC AAG GCC CCC AAG AAT CTC GGC GAC GTG

ATC TAC ACG TTC CGC TAC AGG CGC AGC CTG CCA AAG

GCG ATC CTG GAT TGT CAG CCT ACG GGC GCG TTT TGG

CTT ATC CTC GGC GCC GGC GAC GCC CGC TAT CGT TTC

CGC CTC AGC AAG CTC TGC TAC ATC GAG CCG ACA CCC

GGA CTG CTC GTC AGG AAA ATC CCC GAC GCG ACC CCC

GAG ATC ATC GCT CAG TAT GCG CTC GGC GAC GAG CAA

GCG TTG CTC GCG AAG GTG CGC TAC AAC GGG CTC ATC

GAC ATA TTC CTG GGT ATC ACG GCC TAC AGT CTG CAA

AAC CAT CTT CGG ACG AAG ATC CCG AAC TAC GGG CAG

ATC GAA ATC GAC GAG CTC TAC GTC GGC CTG GAT TCC
```

-continued
```
AAG GGC GCT CAG TTC ATC GTC CCC GTC CAG GCC AAG

GGT GGC AGC GAC CGG CTC GGC GTG ATT CAG ACA ATT

CAG GAC ACG ATC TTC TGC CGA ACT GCC GAA CGA TAC

CGG CAT TGC GTG GCC CGG ACT GTA TCT GCT CAA TTC

ATG GGC GAC GAC GTC ATC GCC ATG TTC GAG CTC TAC

TTC GAC GAA CAT GAC GTC TCG ATC GTG CAG GAG AAA

CAC TAT CGA CTC GTT CCG GCA CGC GAG ATC ACC GGC

TCG GAC TTG GGC ATC TAT CGT TTG TCC TGA
```

Figure 3:
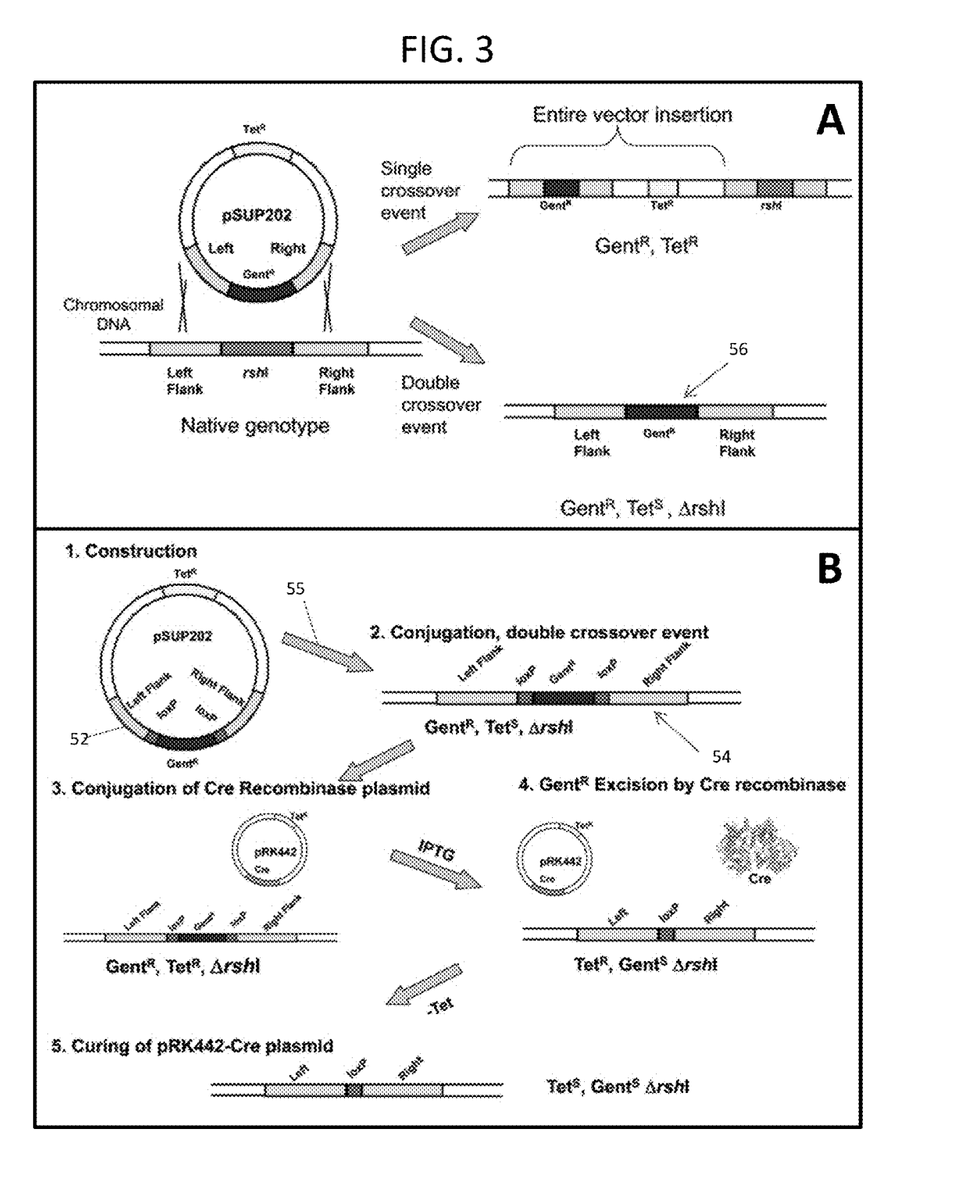
FIGS. 3A and 3B depict a series of circular and linear DNA fragments that diagram the process for producing knockout variants of host organisms and recycling of antibiotic resistance markers, in accordance with features of the present invention.

The rshI-deleted (ΔrshI) mutant of *Rhodobacter* was constructed using the method of gene knockout (FIG. 3). The basic strategy replaces the chromosomal rshI gene sequence with a selectable antibiotic resistance gene (in this case one conferring resistance to Gentamicin; Gm) using the suicide vector pSUP202. The antibiotic resistance marker is then excised via the action of Cre recombinase.

Bacterial Strains

The bacterial strains used in engineering efforts in this study are given in Table 1. *Escherichia (E.) coli* cultures were grown in rich Luria-Bertani (LB) medium. *Rhodobacter (R.) sphaeroides* cultures were grown in rich $^G$YCC medium (Taguchi et al., Biochemistry. 1992; 31:10345-55, incorporated herein by reference). When appropriate, the media were supplemented with Gentamicin (50 µg/ml for *E. coli*; 35 µg/ml *R. sphaeroides*) or tetracycline (15 µg/ml for *E. coli*; 1 µg/ml for *R. sphaeroides*). Kanamycin and spectinomycin are also suitable markers.

Table 1 below lists the specific bacterial strains used.

TABLE 1

| Strain | Description | Source |
|---|---|---|
| *E. coli* | | |
| DH5α | cloning host; F⁻ endA1 glnV44 thi-1 recA1 relA1 gyrA96 deoR nupG Φ80dlacZΔM15 Δ(lacZYA-argF)U169, hsdR17($r_K^-$ $m_K^+$), λ- | Purchased from GIBCO-BRL, now Invitrogen, in Carlsbad, California, catalog number 18265-017. |
| S17-1 | host used for conjugal matings; recA pro hsdR RP4-2-Tc::Mu-Km::Tn7 | Simon et al., Nature Biotechnology, Vol. 1, p. 784-791, 1983, incorporated in its entirety by reference. |
| *R. sphaeroides* | | |
| 2.4.1 | wild-type | ATCC 17023 |
| ΔΔ11 | pucBA (Km$^R$) pufQBALMX (Sp$^R$), derivative of wild-type 2.4.1 | ATCC PTA-5921 |
| ΔrshI | rshI, derivative of ΔΔ11 | Generated from ΔΔ11 using the protocol disclosed herein. |

Construction of Suicide

Plasmid Detail

To construct this plasmid, PCR products of sequences that flank the rshI gene on both sides in the *Rhodobacter* genome (*R. sphaeroides* strain 2.4.1 genomic DNA used; ATCC 17023) and a gene encoding Gentamicin resistance (from pBBR1MCS-5; Genbank Accession Number U25061; Kovach et al., Gene. 1995; 166:175-176) were joined in an overlap extension PCR reaction. The Gentamicin resistance gene was flanked with loxP sequences to facilitate its excision by Cre recombinase in a marker recycling strategy (Marx and Lidstrom, 2002, BioTechniques, 33:1062-1067).

To enable the introduction of the lengthy loxP sequences, an intermediate plasmid construct was required. Gentamicin resistance gene was amplified using primers that encode the loxP sequences (loxGentfwd and loxGentrvs; Table 2). This 858 fragment was cloned into SmaI-digested pBS⁻ (Stratagene). The primers used to amplify the loxP flanking regions and Gm from the pBS⁻ intermediate construct to enable the joining reaction are also listed in Table 2 (RshIFrgmt2Fwd and RshIFrgmt2Rvs). The joined product was cloned non-directionally into a version of pSUP202 ($Ap^R Cm^R Tc^R$) (Simon et al., Bio/Technology. 1983; 1:37-45) containing a modified polylinker—a mobilizable plasmid that cannot be replicated in *R. sphaeroides*—using XhoI and SpeI sites designed into the outer-most primer set, at the ends of the flanking regions, to create pSUP202rshIKO ($Ap^R Tc^R Gm^R$).

cassette was confirmed by PCR with primers, listed in Table 4 (in 5'→3' format), that produce amplicons that bridge the regions between the flanking sequences and the antibiotic resistance cassette.

TABLE 3

Recipe for *R. sphaeroides* medium MR26
Use 20 mL of A, B, and C per L of MR26 medium;
add 1 mL D per L after autoclaving.

| A. | Potassium phosphate buffer: | 1M, pH 6.8, adjusted with KOH or $H_3PO_4$ | |
|---|---|---|---|
| | | $K_2HPO_4$ | 115 g/L |
| | | $KH_2PO_4$ | 44.9 g/L |

TABLE 2

| Gene Amplified | Primer Names | Primer Sequences (5'→3') | Amplicon size (bp) | Notes |
|---|---|---|---|---|
| RSP_3757 | RshIFgmtIFwd | CTGTCTCGAGTGACTCCCT TCGCCGTGTACACTGC SEQ ID NO: 2 | 630 | XhoI at 5' end |
| | RshIFgmtIRvs | GTATAATGTATGCTATACG AAGTTATCAAGATTGTCGT CGCCCCAAGCGC SEQ ID NO: 3 | | Overlaps 5' end of loxP |
| loxP-$Gm^R$-loxP | loxGentFwd | ATAACTTCGTATAGCATAC ATTATACGAAGTTATGACG CACACCGTGGAAACG SEQ ID NO: 4 | 858 | Introduces loxP on the 5'-end of $Gm^R$ |
| | loxGentRvs | ATAACTTCGTATAATGTAT GCTATACGAAGTTATTTAG GTGGCGGTACTTGGGTC SEQ ID NO: 5 | | Introduces loxP on the 3'-end of $Gm^R$ |
| OL-loxP-$Gm^R$-loxP-OL | RshIFrgmt2Fwd | TTGGGGCGACGACAATCTT GGGTCGACTCTAGAGGATC CCC SEQ ID NO: 6 | 898 | Overlaps 3' end of RSP_3757 |
| | RshIFrgmt2Rvs | CGTGTGGTAAATGGCTGAT CGCGAATTCGAGCTCGGTA CCC SEQ ID NO: 7 | | Overlaps 5' end of RSP_3758 |
| RSP_3758 | RshIFgmt3Fwd | GTATAGCATACATTATACG AAGTTATGATCAGCCATTT ACCACACGTAATTGG SEQ ID NO: 8 | 630 | Overlaps 3' end of loxP |
| | RshIFgmt3Rvs | TGTAACTAGTCTGAACAAC GATGCCTGGCATTACG SEQ ID NO: 9 | | SpeI at 3' end |

Construction of Deletion
Strain ΔrshI Detail

Following transfer of pSUP202rshIKO to the *R. sphaeroides* recipient strain ΔΔ11 via conjugation with *E. coli* donor strain S17-1 (Simon et al., ibid), $Gm^R Tc^S$ exconjugants that had lost the rshI gene as a result of a double-crossover event were selected. In brief, matings were performed with small nitrocellulose filter discs placed atop 2XTY agar plates at 37° C. for 3 hours using an equal ratio of donor cells to recipient cells. The mating mixture was removed from the filter in 1 mL of MR26 medium (Table 3) and washed twice in the same.

The entire conjugal reaction was plated on MR26/Gm agar plates. Selection for desired deletion mutants proceeded on rich $^G$YCC agar plates. Routine molecular biology procedures were used as per Sambrook et al., (Molecular cloning: A laboratory manual. 1989. New York. Cold Spring Harbor Press). Replacement of the rshI gene with the $Gm^R$ TABLE 3-continued Recipe for *R. sphaeroides* medium MR26
Use 20 mL of A, B, and C per L of MR26 medium;
add 1 mL D per L after autoclaving.

| B. | Ammonium succinate: | 1M, pH 6.8 Dissolve 118 g succinic acid in 500 mL $H_2O$. Adjust pH to 6.8 with ammonium hydroxide. Add $H_2O$ to 1 L. | |
|---|---|---|---|
| C. | Concentrated base (per L): | Add the following in order: | |
| | | $Na_2EDTA \cdot 2H_2O$ | 11.16 g |
| | | $(NH_4)_6Mo_7O_{24} \cdot 4H_2O$ | 0.0093 g |
| | | $FeSO_4 \cdot 7H_2O$ | 0.099 g |
| | | "Metals 44" | 50 mL |
| | | $MgSO_4$ | 14.5 g |
| | | $CaCl_2$ | 2.5 g |
| Metals 44 (per L): | | $FeSO_4 \cdot 7H_2O$ | 5.0 g |
| | | $Na_2EDTA \cdot 2H_2O$ | 6.5 g |

TABLE 3-continued

Recipe for R. sphaeroides medium MR26
Use 20 mL of A, B, and C per L of MR26 medium;
add 1 mL D per L after autoclaving.

|   |   |   |   |
|---|---|---|---|
|   |   | $ZnSO_4 \cdot 7H_2O$ | 10.9 g |
|   |   | $MnCl_2 \cdot 4H_2O$ | 1.3 g |
|   |   | $CuSO_4 \cdot 5H_2O$ | 0.392 g |
|   |   | $CoCl_2 \cdot 6H_2O$ | 0.200 g |
|   |   | $H_3BO_3$ | 0.114 g |
| D. | Vitamins: | (per L to prepare 1000x stock solution): |   |
|   |   | Nicotinic acid | 3.0 g |
|   |   | Nicotinamide | 3.0 g |
|   |   | Thiamine HCl | 6.0 g |
|   |   | Biotin | 0.12 g |
|   |   | Filter sterilize and store at 4° C. |   |

TABLE 4

Oligonucleotides used in PCR reactions to
confirm allelic exchange of rshI and Gm (5'→3').

| | |
|---|---|
| RshIConfirm1Fwd | CTAGGTGGATCGCTTCGAGGAGGG<br>SEQ ID NO: 10 |
| RshIFgmt1Rvs | GTATAATGTATGCTATACGAAGTTATCAAGAT<br>TGTCGTCGCCCCAAGCGC<br>SEQ ID NO: 11 |
| RshIConfirm3Rvs | GCCATGAAACCGCCACTGCGCCG<br>SEQ ID NO: 12 |
| RshIConfirm4Fwd | CTCTATACAAAGTTGGGCCATACGGG<br>SEQ ID NO: 13 |
| RshIFgmt3Fwd | GTATAGCATACATTATACGAAGTTATGATCAG<br>CCATTTACCACACGTAATTGG<br>SEQ ID NO: 14 |
| RshIConfirm6Rvs | CGCCCCAGACGAATGCAGCCG<br>SEQ ID NO: 15 |

As the final step in the process, a second plasmid encoding the Cre recombinase was transferred to the new deletion strain via conjugation. This plasmid was based on broad-host-range vector pRK442 (Scott et al., 2003, Plasmid, 50: 74-79.). The gene encoding the Cre recombinase was amplified from plasmid pIC-Cre (Addgene; catalog #19131) and was cloned into pRK442 as an EcoRI/PstI fragment downstream of the lac promoter. Oligonucleotides used in the amplification of the Cre recombinase are shown in Table 5. Plasmid pRK442-Cre was transferred to the ΔrshI knockout strain via conjugal mating and was selected on agar plates containing tetracycline. Synthesis of the recombinase was induced by 1 mM IPTG to enable excision of the Gentamicin resistance gene facilitated by the engineered loxP sites. Another round of selection produced candidate colonies that lacked resistance to gentamicin. Again, the presence of the rshI knockout in the absence of the Gentamicin-resistance cassette was confirmed using PCR with the same diagnostic primers (Table 4). Following repeated subculturing, in the absence of tetracycline to 'cure' the new deletion strain of the plasmid encoding the Cre recombinase (FIG. 3), construction of the ΔrshI strain was complete.

TABLE 5

Oligonucleotides used in PCR reactions to
amplify the gene encoding Cre recombinase (5'→3').

| | |
|---|---|
| EcoCreFwd | CTGTGAATTCGGAGAAGCTGAATGTCCAATTT<br>ACTGACCGTACACC<br>SEQ ID NO: 16 |
| PstCreRvs | TGTACTGCAGCTAATCGCCATCTTCCAGCAGG<br>SEQ ID NO: 17 |

Example 2

Chemical Transformation

Cells were grown in rich medium (GYCC) and were harvested in early- to mid-log phase. The cells were washed with ice-cold 0.5 M Tris-Cl (pH 7.2), then were re-suspended in ice-cold 0.1 M Tris (pH 7.2)/0.2 M $CaCl_2$ to a final concentration of ~$8 \times 10^{10}$ cells/ml. An 0.2 ml aliquot was transferred to a tube on ice and was mixed with 1 µg of plasmid DNA, followed by 0.2 ml 40% PEG6000 in 0.1 M Tris (pH 7.2). Tubes that contained cells but no DNA served as negative controls. The tubes were kept on ice for 10 min, then were heat-shocked for 2 min at 35° C. GYCC medium (1 ml) was then added and the tubes were incubated at 35° C. for 20 min, then an additional 3 ml of GYCC was added and the cells were cultured at 35° C. for an outgrowth period of between about 4 and 26 hours.

Cells were then pelleted and were plated to GYCC agar containing tetracycline (1 µg/ml) to select for the presence of the plasmid. Plates were monitored for the appearance of transformed colonies following incubation at 33° C. for 2-4 days.

Figure 4:
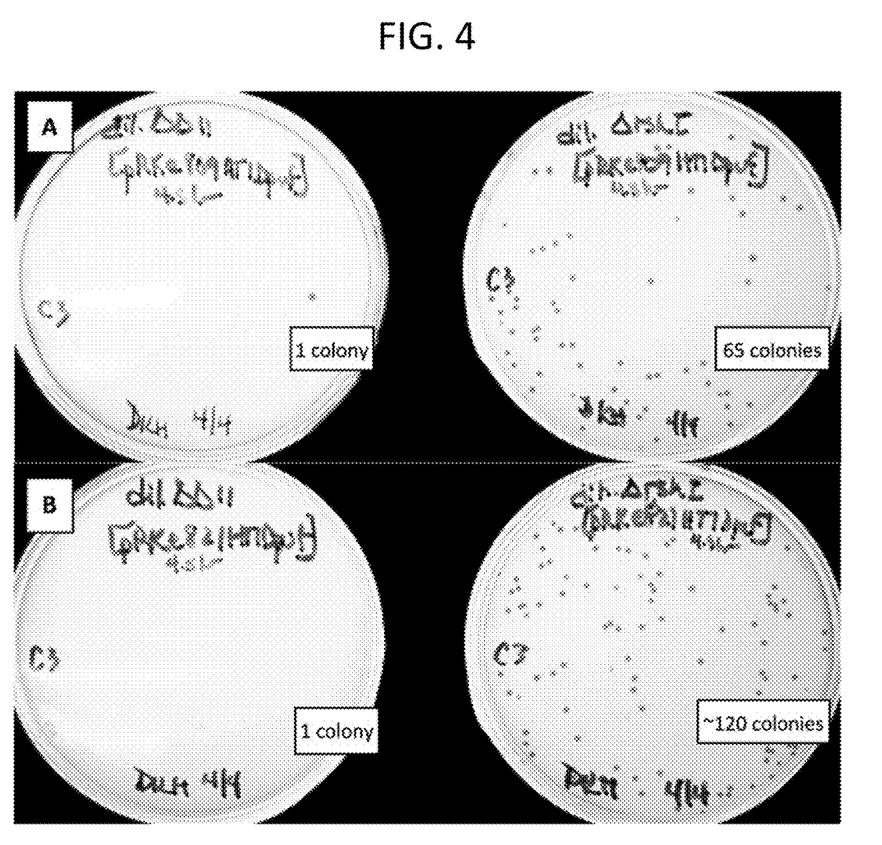
FIGS. 4A and 4B depict efficiencies of chemical transformation, in accordance with features of the present invention.

Competent cells of the unmodified host strain ΔΔ11 and newly-deleted strain ΔrshI were incubated with expression plasmids encoding E. coli membrane protein target genes (e809 and e821). Both of these expression plasmids have seven RshI sites, which is evident from the very low transformation frequency observed with ΔΔ11. The efficacy of the deletion in promoting transformability in the ΔrshI host strain is depicted in FIG. 4 which shows the increase in number of transformants. Specifically, FIG. 4 exhibits transformation of chemically-competent cells of R. sphaeroides host strains with expression plasmids for E. coli membrane protein targets e809 (panel A) and e821 (panel B). The ΔrshI strain (A, right; B, right) is newly-deleted for an endogenous restriction enzyme and serves as a more favorable host [as compared to unmodified strain ΔΔ11 (A, left; B, left)] because it does not destroy foreign DNA.

This experiment also compared results obtained with different periods of outgrowth (4.5 hr or 26 hr) and determined that similar numbers of transformants were obtained following the short outgrowth period. Thus, the transformation protocol can be completed within one workday, simplifying the implementation of the Rhodobacter expression system and increasing the efficiency of the experiment.

Example 3

Electroporetic Transformation

Cells were grown in GYCC medium and harvested in early- to mid-log phase. The cell pellet was washed three times in successively smaller volumes of ice-cold distilled, deionized $H_2O$ and finally in ice-cold 10 percent glycerol. The final pellet was resuspended in ice-cold 10 percent glycerol to a concentration of ~$5-8 \times 10^{10}$ cells/ml. For electroporation, a 40 μl aliquot of cells was mixed in a microfuge tube on ice with 100 ng plasmid DNA. Tubes that contained cells but no DNA served as controls; an additional negative control comprised a cell/DNA mixture that received no pulse. The mixture was transferred to a chilled 2-mm electroporation cuvette and subjected to one electrical pulse at the following settings: 2500 V, 25 μF, 200 ohm. The time constant for the pulse was approximately 10 msec. The cuvette was returned immediately to ice and 1 ml GYCC medium was added. The cells were then transferred to a culture tube and were incubated at 35° C. with slow shaking for a four hour outgrowth period. The entire culture was then pelleted and plated to GYCC agar containing tetracycline (1 μg/ml). Plates were incubated at 33° C. for several days.

Figure 5:
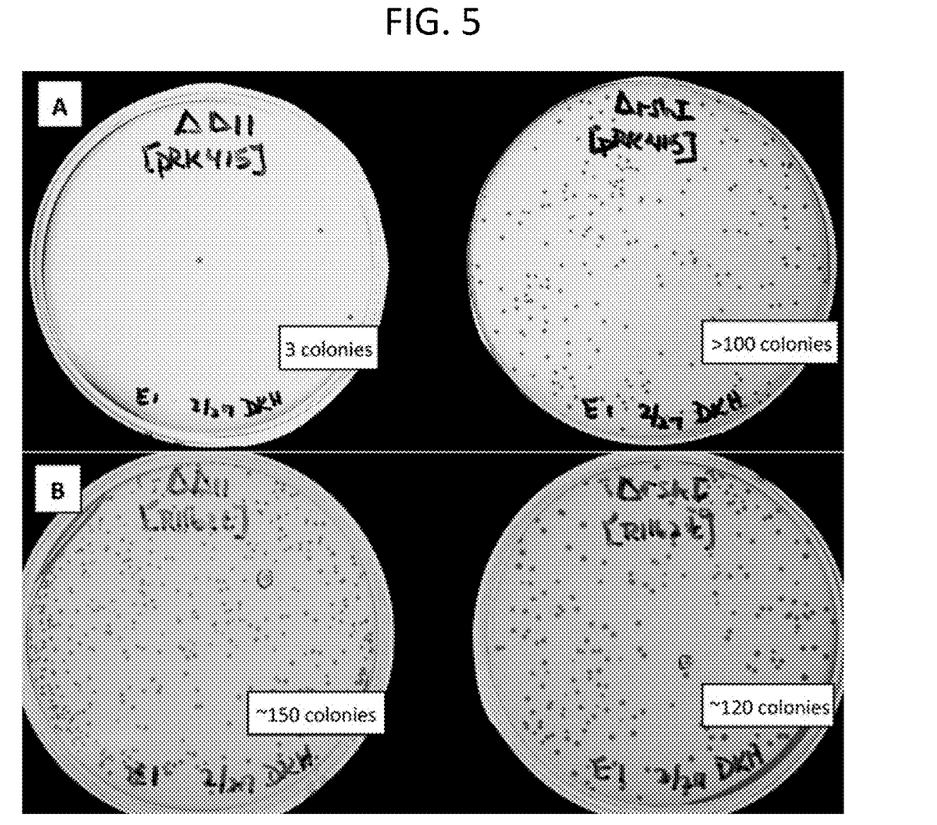
FIGS. 5A and 5B depict efficiencies of electroporetic transformation, in accordance with features of the present invention.

As depicted in FIG. 5, this experiment compares the abilities of electrocompetent cells of two different host strains to take up plasmids that contain (A) or lack (B) RshI sites. Panel A: pRK415 has four RshI sites, thus the ΔrshI strain (right) serves as a more favorable host when compared to unmodified strain ΔΔ11 (left) because it does not destroy foreign DNA. Panel B: Plasmid R1162t does not have any RshI sites and can be used to transform both host strains with similar efficiency.

While no difference in transformation efficiency is noted with the RshI-less plasmid R1162, the transformation efficiency for the ΔrshI host strain with RshI-containing pRK415 is markedly improved over that of the ΔΔ11 host. The transformation efficiency of the ΔrshI strain with RshI-containing plasmids guarantees that routine, simple laboratory methods will result in the generation of a recombinant *Rhodobacter* strain. The transformation of ΔΔ11 with plasmids of this type is so inefficient that chemical and electroporetic transformation methods cannot ensure production of such strains.

A myriad of existing vectors are suitable in shuttling target genes to the host strains, those vectors including but not limited to RK2, pRK404, pRK415, pBBR1, pRK290, pRK310, RSF1010, and the derivatives of each of these vectors.

Example 4

Expression of Heterologous Proteins

In creating the knockout expression strain that was easy to transform, it was important to check that all of the engineering and passaging and selection did not alter any aspects of the strain that are deemed essential for its role as an expression host for membrane proteins. The ability of the ΔrshI strain to serve as a host for heterologous expression of membrane proteins was evaluated by comparing yields of expressed proteins in ΔrshI and its parent strain ΔΔ11. Here, we show a direct comparison of two membrane proteins (e809 and e821). The membrane proteins are foreign to *Rhodobacter*, having been derived from *E. coli*, and were previously shown to express to high levels in production strategies based upon ΔΔ11 ('216). In these two examples, expression vectors carrying either e809 or e821 genes were transferred to the ΔrshI host strain via electroporation; the ΔΔ11 expression strains were generated previously using bi-parental conjugation. Small-scale cultures of the ΔrshI [pRKe809HT1Dpuf] and ΔrshI[pRKe821 HT1Dpuf], ΔΔ11 [pRKe809HT1Dpuf], and ΔΔ11[pRKe821HT1Dpuf] expression strains were grown under chemoheterotrophic conditions (dark, semi-aerobic, 33 C) that coordinate induction of both the foreign membrane protein gene and the intracytoplasmic membranes of the host strain that serve to sequester the newly-expressed membrane proteins. The cells were lysed, and membranes were harvested and subjected to SDS-PAGE.

Figure 6:
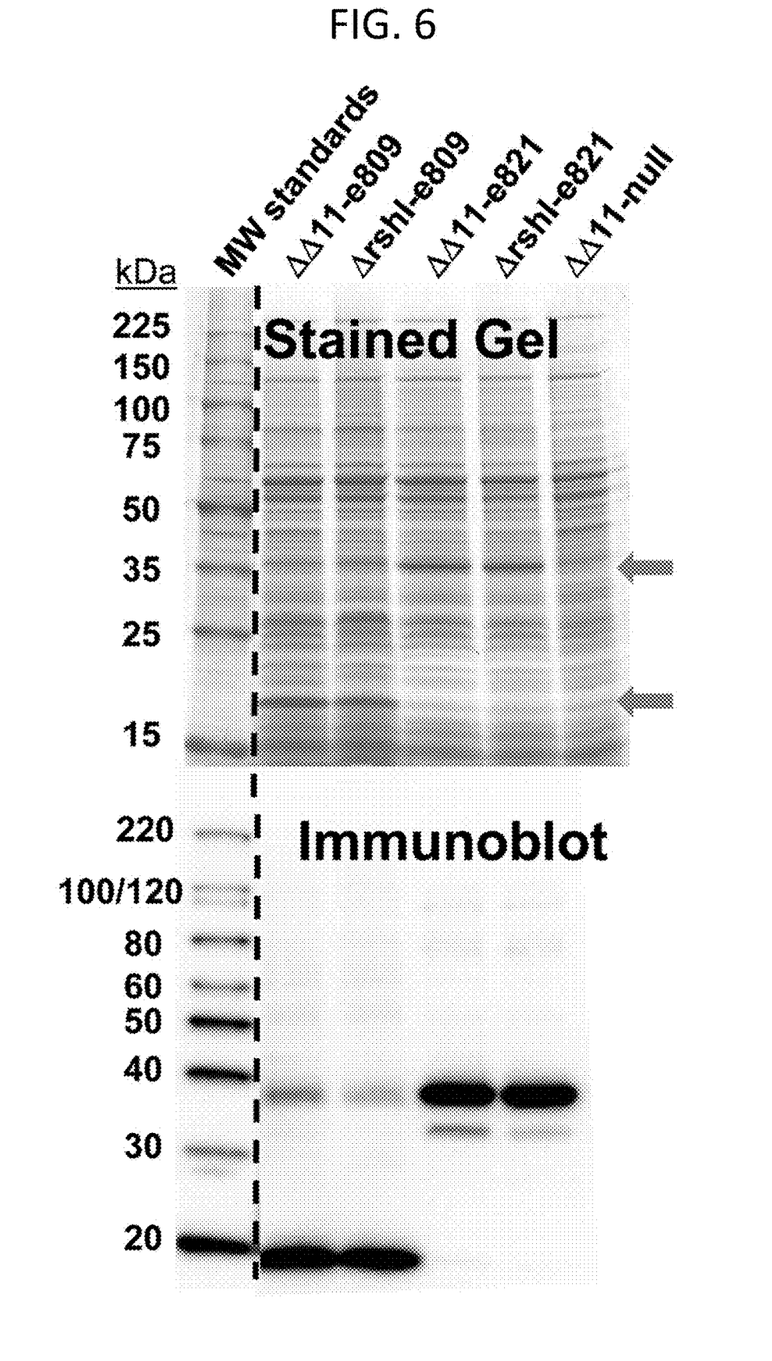
FIG. 6 compares yields for heterologous expression of two membrane proteins in the parent host strain, ΔΔ11, and the newly engineered strain, ΔrshI.

FIG. 6 compares yields obtained for these two membrane proteins when they were expressed in either the ΔrshI host or the ΔΔ11 host. Replicate gels were prepared for either staining with Coomassie Brilliant Blue (upper panel) or immunoblotting for antibody-mediated detection of the expressed polyhistidine-tagged heterologous proteins (lower panel). Data in FIG. 6 show membrane localized expression of these two target proteins. Both the stained gel (arrows) and the immunoblot indicate that expression is identical in the two host strains. The results show that the newly-constructed ΔrshI strain is effective as a host strain for expression of heterologous membrane proteins and that there is no obvious effect of the rshI deletion on the yield of expression as compared to the yield obtained with its parent strain ΔΔ11. With quantification that is possible by comparison of signal intensities to those of standards produced at known levels, the expression of both target genes in both host strains exceeds 10 mg/L. Surprisingly and unexpectedly, the inventors found that ΔrshI is as good an expression host as ΔΔ11 and deletion of parts of its restriction-modification system has no impact on membrane protein production, as expected from trends observed with similar expression hosts of other organisms where restriction-modification systems have been engineered.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. An organism for producing and sequestering heterologous biological moieties, wherein the organism is *R. sphaeroides*, and wherein the genome of the organism codes for intracytoplasmic membranes but is modified to not code for the restriction enzyme RshI, the organism created by the method comprising:
   (a) providing *R. sphaeroides* wherein the genome of the *R. sphaeroides* codes for the intracytoplasmic membranes;
   (b), modifying the genome of said *R. sphaeroides* a first time to not code for the restriction enzyme RshI, and
   (c) modifying the genome of said *R. sphaeroides* a second time to produce at least one heterologous membrane protein and to sequester said at least one heterologous membrane protein within said intracytoplasmic membranes.

2. The organism of claim 1 wherein modifying the genome a first time comprises deleting the gene RSP_3759 from said *R. sphaeroides*' genome.

3. The organism of claim 1 wherein the *R. sphaeroides* is modified the first time so as to be capable of receiving replicatable and nonreplicatable vectors to immediately produce an expression strain.

4. The organism of claim 1 wherein the genome is modified the second time using electroporation.

5. The organism of claim 1 wherein the genome is modified the second time using chemical transformation.

* * * * *

```
                            SEQUENCE LISTING

<160> NUMBER OF SEQ ID NOS: 17

<210> SEQ ID NO 1
<211> LENGTH: 858
<212> TYPE: DNA
<213> ORGANISM: Rhodobacter sphaeroides

<400> SEQUENCE: 1
atggctgatc ctgaacccga gaacgtttcg gcagaagccc aggcggccgt cacttccgcc    60
gagccgaaga cattgaacgc ctatcaggcg atcatcgtcg acatcttcca acggttctat   120
cggccgggca tggaggagtt cgagttcggc cgcgaggaaa tctacgaggc cgccgtcagg   180
acgggcgtca aggcccccaa gaatctcggc gacgtgatct acacgttccg ctacaggcgc   240
agcctgccaa aggcgatcct ggattgtcag cctacgggcc gcttttggct tatcctcggc   300
gccggcgacg cccgctatcg tttccgcctc agcaagctct gctacatcga gccgacaccc   360
ggactgctcg tcaggaaaat ccccgacgcg accccgaga tcatcgctca gtatgcgctc    420
ggcgacgagc aagcgttgct cgcgaaggtg cgctacaacc ggctcatcga catattcctg   480
ggtatcacgg cctacagtct gcaaaaccat cttcggacga agatcccgaa ctacgggcag   540
atcgaaatcg acgagctcta cgtcggcctg gattccaagg gcgctcagtt catcgtcccc   600
gtccaggcca agggtggcag cgaccggctc ggcgtgattc agacaattca ggacacgatc   660
ttctgccgaa ctgccgaacg ataccggcat tgcgtggccc ggactgtatc tgctcaattc   720
atgggcgacg acgtcatcgc catgttcgag ctctacttcg acgaacatga cgtctcgatc   780
gtgcaggaga aacactatcg actcgttccg gcacgcgaga tcaccggctc ggacttgggc   840
atctatcgtt tgtcctga                                                 858

<210> SEQ ID NO 2
<211> LENGTH: 35
<212> TYPE: DNA
<213> ORGANISM: Rhodobacter sphaeroides

<400> SEQUENCE: 2
ctgtctcgag tgactccctt cgccgtgtac actgc                               35

<210> SEQ ID NO 3
<211> LENGTH: 50
<212> TYPE: DNA
<213> ORGANISM: Rhodobacter sphaeroides

<400> SEQUENCE: 3
gtataatgta tgctatacga agttatcaag attgtcgtcg ccccaagcgc                50

<210> SEQ ID NO 4
<211> LENGTH: 53
<212> TYPE: DNA
<213> ORGANISM: Rhodobacter sphaeroides

<400> SEQUENCE: 4
ataacttcgt atagcataca ttatacgaag ttatgacgca caccgtggaa acg            53
```

<210> SEQ ID NO 5
<211> LENGTH: 55
<212> TYPE: DNA
<213> ORGANISM: Rhodobacter sphaeroides

<400> SEQUENCE: 5
ataacttcgt ataatgtatg ctatacgaag ttatttaggt ggcggtactt gggtc      55

<210> SEQ ID NO 6
<211> LENGTH: 41
<212> TYPE: DNA
<213> ORGANISM: Rhodobacter sphaeroides

<400> SEQUENCE: 6
ttggggcgac gacaatcttg ggtcgactct agaggatccc c                     41

<210> SEQ ID NO 7
<211> LENGTH: 41
<212> TYPE: DNA
<213> ORGANISM: Rhodobacter sphaeroides

<400> SEQUENCE: 7
cgtgtggtaa atggctgatc gcgaattcga gctcggtacc c                     41

<210> SEQ ID NO 8
<211> LENGTH: 53
<212> TYPE: DNA
<213> ORGANISM: Rhodobacter sphaeroides

<400> SEQUENCE: 8
gtatagcata cattatacga agttatgatc agccatttac cacacgtaat tgg        53

<210> SEQ ID NO 9
<211> LENGTH: 35
<212> TYPE: DNA
<213> ORGANISM: Rhodobacter sphaeroides

<400> SEQUENCE: 9
tgtaactagt ctgaacaacg atgcctggca ttacg                            35

<210> SEQ ID NO 10
<211> LENGTH: 24
<212> TYPE: DNA
<213> ORGANISM: Rhodobacter sphaeroides

<400> SEQUENCE: 10
ctaggtggat cgcttcgagg aggg                                        24

<210> SEQ ID NO 11
<211> LENGTH: 50
<212> TYPE: DNA
<213> ORGANISM: Rhodobacter sphaeroides

<400> SEQUENCE: 11
gtataatgta tgctatacga agttatcaag attgtcgtcg ccccaagcgc             50

<210> SEQ ID NO 12
<211> LENGTH: 23
<212> TYPE: DNA
<213> ORGANISM: Rhodobacter sphaeroides

<400> SEQUENCE: 12
gccatgaaac cgccactgcg ccg                                         23

```
<210> SEQ ID NO 13
<211> LENGTH: 26
<212> TYPE: DNA
<213> ORGANISM: Rhodobacter sphaeroides

<400> SEQUENCE: 13
ctctatacaa agttgggcca tacggg                                        26

<210> SEQ ID NO 14
<211> LENGTH: 53
<212> TYPE: DNA
<213> ORGANISM: Rhodobacter sphaeroides

<400> SEQUENCE: 14
gtatagcata cattatacga agttatgatc agccatttac cacacgtaat tgg          53

<210> SEQ ID NO 15
<211> LENGTH: 21
<212> TYPE: DNA
<213> ORGANISM: Rhodobacter sphaeroides

<400> SEQUENCE: 15
cgccccagac gaatgcagcc g                                             21

<210> SEQ ID NO 16
<211> LENGTH: 46
<212> TYPE: DNA
<213> ORGANISM: Rhodobacter sphaeroides

<400> SEQUENCE: 16
ctgtgaattc ggagaagctg aatgtccaat ttactgaccg tacacc                  46

<210> SEQ ID NO 17
<211> LENGTH: 32
<212> TYPE: DNA
<213> ORGANISM: Rhodobacter sphaeroides

<400> SEQUENCE: 17
tgtactgcag ctaatcgcca tcttccagca gg                                 32
```